(12) United States Patent
Miracle et al.

(10) Patent No.: US 6,544,945 B1
(45) Date of Patent: Apr. 8, 2003

(54) CYCLIC PRO-PERFUMES HAVING MODIFIABLE FRAGRANCE RAW MATERIAL ALCOHOL RELEASE RATES

(75) Inventors: Gregory Scot Miracle, Hamilton, OH (US); Kenneth Nathan Price, Wyoming, OH (US); Lon Montgomery Gray, Florence, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/622,888

(22) PCT Filed: Feb. 8, 1999

(86) PCT No.: PCT/US99/02732
§ 371 (c)(1),
(2), (4) Date: Aug. 23, 2000

(87) PCT Pub. No.: WO99/43667
PCT Pub. Date: Sep. 2, 1999

Related U.S. Application Data

(60) Provisional application No. 60/075,708, filed on Feb. 24, 1998.

(51) Int. Cl.[7] .................................................. A61K 7/46
(52) U.S. Cl. ............................. 512/27; 512/2; 512/12; 549/200; 549/346; 549/347; 549/356; 549/357
(58) Field of Search ............................... 512/2, 12, 27; 549/200, 346, 347, 356, 357

(56) References Cited

U.S. PATENT DOCUMENTS 4,211,674 A * 7/1980 Lenselink ..................... 106/10
4,761,489 A * 8/1988 Gramltch et al. ............. 512/12
5,231,197 A   7/1993 Khouri et al. ............... 549/372

FOREIGN PATENT DOCUMENTS

| EP | 067 361 | 12/1982 | ......... C07D/317/34 |
| EP | 518 428 | 12/1992 | ............. C08F/4/46 |
| GB | 2018251 | 10/1979 | ......... C07D/319/08 |
| WO | WO 98/47478 | 10/1998 | ............ A61K/7/46 |

OTHER PUBLICATIONS

Bouchra et al.: "A new method of Orthoesterification" Carbohydrate Research, vol. 267, No. 2, 1995, pp 227–237) XP002104820, Amsterdam NL.

Soulier et al.: "Synthese de Quelques Alcoxy–2 et Aryloxy–2 Dioxannes 1,3", Journal of Hterocyclic Chemistry, vol. 13, No. 5, 1976 (pp 1125–1128), XP002104819, Provo, US.

Chemical Abstracts, vol. 114, No. 7, 1991, Columbus, OH, USA, Abstract No. 62170m, Chatani, N. et al.: "Dicobalt Octacarbonyl Catalysed Reaction of Cyclic Ortho–Esters" (p. 698) Col. 2; XP002104821.

* cited by examiner

*Primary Examiner*—Jill Warden
*Assistant Examiner*—Monique T. Cole
(74) *Attorney, Agent, or Firm*—James F. McBride; Richard S. Echler, Sr.; Kim W. Zerby

(57) ABSTRACT

The present invention relates to cyclic pro-perfumes comprising a moiety derived from a fragrance raw material alcohol. Such cyclic perfumes may contain dioxolane and glucosyl orthesters that are suitable for use in delivering enhanced fragrance longevity to human skin.

13 Claims, No Drawings

CYCLIC PRO-PERFUMES HAVING MODIFIABLE FRAGRANCE RAW MATERIAL ALCOHOL RELEASE RATES

CROSS REFERENCE TO RELATED APPLICATIONS

This application is a national stage entry under 35 U.S.C. §371 of PCT/US99/02732, filed Feb. 8, 1999, which claims the benefit of U.S. Provisional Application No. 60/075,708 filed Feb. 24, 1998 (now abandoned).

FIELD OF THE INVENTION

The present invention relates to cyclic pro-perfumes capable of releasing at least one fragrance raw material alcohol, preferably a tertiary fragrance raw material alcohol. The novel pro-perfumes of the present invention can be modified by the formulator to control the rate at which the fragrance raw material alcohol is released once the material is applied, for example, to human skin.

BACKGROUND OF THE INVENTION

Humans have applied scents and fragrances to their skin since antiquity. Originally these aesthetically pleasing materials were commonly isolated in raw form as resins, gums or essential oils from natural sources, inter alia, the bark, roots, leaves and fruit of indigenous plants. These resins, gums, and oils were directly applied to the body or diluted with water or other solvent, including in some cases, wine. With the advent of modern chemistry, individual components responsible for the odor properties of these resins, gums and oils were isolated and subsequently characterized. Modern perfumery involves the artful compounding of fragrance materials to achieve novel fragrance compositions having defined "characteristics".

Many modem fragrances are no longer derived from natural sources but are synthesized by modern chemical methods as highly pure fragrance raw materials (FRM). These FRM's are currently formulated to produce fine perfumes, colognes, eau de toilettes, after-shave lotions, and other personal fragrance compositions. Those skilled in the art of preparing these fragrance-containing compositions have categorized fragrances into three types based on their relative volatility; top, middle, and base notes.

Top, middle, and base notes each serve a different purpose in the blending of fragrances and when properly formulated produce a "balanced fragrance" composition. Based on volatility, these notes are described by those skilled in the art as: the base notes having the most long lasting aroma; the middle notes, have a medium volatility; and the top notes are the most volatile. Key to successfully formulating a fragrance-containing composition is the precise balance between these three groups of materials producing a fragrance-containing composition that diffuses during its evaporation in a manner which has an aesthetic quality.

It has been the goal of those skilled in the art of perfumes and fragrances to provide aesthetically pleasant odor compositions wherein the initial top, middle, and base note balance is maintained for an extended period of time. Due to the uneven rate of evaporation of the components which comprise a fine perfume or fragrance, the initial fragrance may be quite different than the aroma perceived several hours later. This problem is solved in many different ways by the user. One method is to "load up" on the perfume initially and rely on the natural evaporation rate to diminish the fragrance to a suitable level several hours later when the desired effect is needed. Another method which is used is to continually renew the fragrance by reapplying small amounts of the perfume to the skin at short time intervals. Neither of these solutions is adequate to overcome the diminishing level of top and middle notes over time. In fact, base notes which are present over a protracted period by virtue of their low volatility, begin to accumulate with each "re-freshing" of perfume. After some time these base notes overwhelm the other fragrance notes and destroy the original fragrance balance.

However, despite these artful approaches and compensating for the physical properties of perfume ingredients, formulators have not been able to well control the rate at which fragrance raw materials, especially fragrance raw material alcohols, are released when applied, for example, on human skin, hair, etc. Therefore, there has been a long felt need for a means of releasing at least one fragrance raw material alcohol, preferably tertiary alcohols, at a controllable rate.

It has now been surprisingly discovered that the novel cyclic pro-perfumes, which are the subject matter of the present invention, can not only release fragrance raw material alcohols but can be modified to release said alcohols within a range of time desirable to the formulator. In addition, the cyclic pro-perfumes described herein are capable of delivering highly desirable tertiary alcohols.

SUMMARY OF THE INVENTION

The present invention meets the aforementioned needs in that it has been surprisingly discovered than certain cyclic pro-perfumes can be modified to release their fragrance raw material alcohols at variable rates after being exposed to an acid milieu inter alia human skin.

A first aspect of the present invention relates to cyclic pro-perfumes capable of releasing at least one fragrance raw material alcohol, said pro-perfumes having the formula:

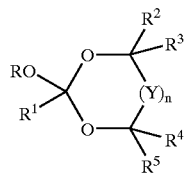

wherein —OR is a unit derived from a fragrance raw material alcohol; $R^1$ is hydrogen, $C_1$–$C_{22}$ alkyl, $C_1$–$C_{22}$ alkenyl, $C_6$–$C_{12}$ aryl, $C_6$–$C_{22}$ alkyleneraryl, $C_3$–$C_{20}$ substituted or unsubstituted alkyleneoxyalkyl, and mixtures thereof; $R^2$, $R^3$, $R^4$, and $R^5$ are each independently selected from hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alky, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkyleneraryl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or any two $R^2$, $R^3$, $R^4$, or $R^5$ can be taken together to form a fused ring or spiroannulated ring having from 3 to 8 carbons and optionally one or more heteroatoms in said ring, said ring is optionally further substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof, Y is —$CR^6R^7$—, C=O, and mixtures thereof, wherein $R^6$ and $R^7$ are independently hydrogen, hydroxyl, nitro, nitrilo, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or $R^6$ and $R^7$ can be taken together to form a spiroannulated ring or taken together with any $R^2$, $R^3$, $R^4$, or $R^5$ to form a fused ring, said spiroannulated or fused ring having from 3 to 8 carbons and optionally one or more heteroatoms in said ring, said ring further optionally substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; n is from 0 to 3.

The present invention also relates to fine fragrance compositions inter alia perfumes, colognes, after shaves, and eau de toilettes comprising said cyclic pro-perfumes. In addition, personal care and personal hygiene articles may comprise the cyclic pro-perfumes described herein. Non-limiting examples of these personal care items include deodorants, body lotions or creams, sun tan lotions, and shampoos.

The present invention also relates to a fragrance delivery system which comprises at least one cyclic pro-perfume as described herein. Preferably said fragrance delivery system delivers at least one tertiary fragrance raw material alcohol. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to cyclic pro-perfumes capable of releasing at least one fragrance raw material alcohol. Surprisingly, the cyclic pro-perfumes of the present invention are capable of releasing in a controlled manner desirable tertiary perfume raw material alcohols inter alia linalool, ethyllinalool, dihydromyrcenol, and tetrahydrolinalool.

The pro-perfumes of the present invention are essentially orthoesters. Orthoesters, in general, may be considered to be "acetals" of carboxylic acid esters which can be formed by the reaction of an ester with two equivalents of alcohol. Treatment of orthoesters with sufficient acid catalyst in the presence of moisture results in the "reversion" of orthoesters back into a mixture of ester and alcohol. In the instance where the ester alcohol is not the same as the orthoester forming alcohol, and depending upon the structure and reactivity of the orthoester components, one of the alcohols released from the reversion reaction may be the original ester alcohol resulting in one of the "orthoester forming" alcohols now comprising the ester. In this instance, "transesterification" has occurred.

Without wishing to be limited by theory, the release rate of the fragrance raw material alcohol from the cyclic orthoesters of the present invention may be controlled, for example, by adjusting, separately or in combination, either the relative basicity of the orthoester oxygen atoms in the cyclic moiety or the torsional ring strain of the resulting cyclic orthoesters. One result of these adjustments is to provide increased or decreased ring opening kinetics and thereby a means for regulating the release rate of the fragrance raw material alcohol.

Cyclic Pro-perfumes

The cyclic pro-perfumes of the present invention have the formula:

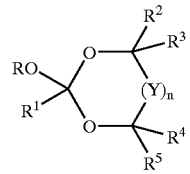

wherein the moiety —OR is derived from a fragrance raw material alcohol having the general formula ROH. Non-limiting examples of fragrance raw material alcohols which can be suitably released by the cyclic pro-perfumes of the present invention include 2,4-dimethyl-3-cyclohexene-1-methanol (Floralol), 2,4-dimethyl cyclohexane methanol (Dihydro floralol), 5,6-dimethyl-1-methylethenylbicyclo-[2.2.1]hept-5-ene-2-methanol (Arbozol), 2,4,6-trimethyl-3-cyclohexene-1-methanol (Isocyclo geraniol), 4-(1-methylethyl)cyclohexanemethanol (Mayol), α-3,3-trimethyl-2-norborane. methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.]hept-2-ene-2-ethanol (nopol), 2-(4-methylphenoxy)ethanol, 3,3-dimethyl-$\Delta^2$-β-norbornane ethanol, 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl4-(2,2,3-trimethyl-cyclopent-3-enyl)-2-buten-1-ol, 3-methyl-2-buten-1-ol, 2-methyl4-(2,2,3-trimethyl-3-cyclopenten-1-yl)-2-buten-1-ol, 3-hydroxy-2-butanone, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)butan-2-one, 3-methyl-pentanol, 3-methyl-3-penten-1-ol, 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0(2,6)]hept-3-yl)-2-penten-1-ol (santalol), 4-methyl-1-phenyl-2-pentanol, (1-methyl-bicyclo [2.1.1]hepten-2-yl)-2-methylpent-1-en-3-ol, 3-methyl-1-phenylpentan-3-ol, 1,2-dimethyl-3-(1-methylethenyl) cyclopentan-1-ol, 2-isopropyl-5-methyl-2-hexenol, cis-3-hexen-1-ol, trans-2-hexen-1-ol, 2-isoproenyl-4-methyl4- hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl4-isopropenycyclohex-6-en-2-ol (carvenol), 6-methyl-3-isopropenylcyclohexan-1-ol, 1-methyl4-iso-propenylcyclohexan-3-ol, 4-isopropyl-1-methylcyclohexan-3-ol, 4-tert-butylcyclo-hexanol, 2-tert-butylcyclohexanol, 2-tert-butyl4-methylcyclohexanol, 4-isopropyl-cyclohexanol, 4-methyl-1-(1-methylethyl)-3-cyclohexen-1-ol, 2-(5,6,6-trimethyl-2-norbornyl) cyclohexanol, isobornylcyclohexanol, 3,3,5-trimethylcyclohexanol, 1-methyl-4-isopropylcyclohexan-3-ol, 1,2-dimethyl-3-(1-methylethyl)cyclohexan-1-ol, heptanol, 2,4-dimethylheptan-1-ol, 2,4-dimethyl-2,6-heptandienol, 6,6-dimethyl-2-oxymethylbicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethy-3-hydroxy-2-methylenebicyclo[3.1.1]heptane, 1,7,7-trimethylbicyclo[2.2.1]heptan-2-ol, 2,6-dimethylheptan-2-ol, 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-1,6-octadien-3-ol (linalool), 3,7-dimethyloctan-1-ol (pelagrol), 3,7-dimethyloctan-3-ol (tetrahydrolinalool), 2,4-octadien-1-ol, 3,7-dimethyl-6-octen-3-ol, 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol (ethyllinalool), decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linallol), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol, 3,7,11,15-tetramethylhexadec-2-en-1-ol (phytol), 3,7,11,15-tetramethylhexadecl-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-orthohydroxy benzoate, ethyl 2-hydroxy-benzoate, methyl 2,4-dihydroxy-3,6-dimethylbenzoate, 3b-hydroxy-5-methoxy-1-methylbenzene, 2-tert-butyl-4-methyl-1-hydroxybenzene, 1-ethoxy-2-hydroxy4-propenylbenzene, 4-hydrozytoluene, 4-hydroxy-3-methoxybenzaldehyde, 2-ethoxy4-hydroxybenzaldehyde, decahydro-2-naphthol, 2,5,5-trimethyl-octahydro-2-naphthol, 1,3,3-trimethyl-2-norbomanol (fenchol), 3a,4,5,6,7,7a-hexahydro-2,4-dimethyl4,7-methano-1H-inden-5-ol, 3a,4,5,6,7,7a-hexahydro-3,4-dimethyl4,7-methano-1H-inden-5-ol, 2-methyl-2-vinyl-5-(1-hydroxy-1-methylethyl) tetrahydrofuran, β-caryophyllene alcohol, and mixtures thereof Preferred fragrance raw material alcohols are tertiary alcohols inter alia 3,7-dimethyl-1,6-octadien-3-ol (linalool), 3,7-dimethyloctan-3-ol (tetrahydrolinalool), 3,7-dimethyl-1,6-nonadien-3-ol (ethyllinalool), and 2,6-dimethyl-7-octen-2-ol (dihydromyrcenol).

$R^1$ is hydrogen, $C_1$–$C_{22}$ alkyl, $C_1$–$C_{22}$ alkenyl, $C_6$–$C_{12}$ aryl, $C_6$–$C_{22}$ alkylenearyl, $C_3$–$C_{20}$ substituted or unsubstituted alkyleneoxyalkyl,. and mixtures thereof Preferably $R^1$ is hydrogen, $C_1$–$C_4$ alkyl, $C_7$–$C_{10}$ alkylenearyl; more preferably hydrogen, methyl, ethyl, propyl, iso-propyl, t-butyl, phenyl, substituted phenyl, benzyl and substituted benzyl.

$R^2$, $R^3$, $R^4$, and $R^5$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof. In addition, any two $R^2$, $R^3$, $R^4$, or $R^5$ units can be taken together to form a fused ring cyclic pro-perfume having from 3 to 8 carbon atoms and optionally one or more heteroatoms in the ring. An example of a fused ring cyclic pro-perfume includes the general formulae:

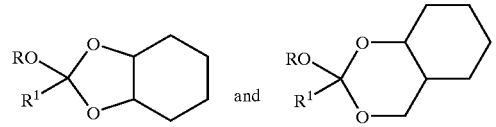

The fused rings may also optionally comprise one or more heteroatoms, preferably oxygen, nitrogen, sulfur and mixtures thereof An example of a fused ring cyclic pro-perfume comprising a heteroatom has the formula:

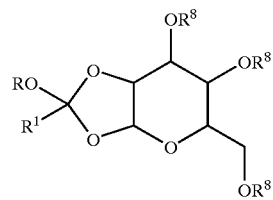

wherein $R^8$ is independently hydrogen, $C_1$–$C_{22}$ alkyl, hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, or one or more saccharide units. Non-limiting examples of saccharide units according to the present invention include erythrose, threose, arabinose, ribose, lysose, xylose, glucose, mannose, allose, altrose, talose, galactose, idose, gulose, fiuctose, and combinations thereof. The saccharides of the present invention are preferably in the pyranose (closed ring) form, however, when in solution, an equilibrium may exist wherein some of the material may exist in the non-preferred ring opened form. Any number of saccharides can be linked together. For example, oligosaccharide—two or three saccharides or polysaccharides—more than three saccharides, are suitable for use in the present invention.

The cyclic pro-perfumes of the present invention further comprise spiroannulated rings having from 3 to 8 carbon atoms and optionally one or more heteroatoms in the ring, examples of which have the general formulae:

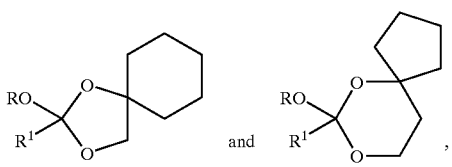

wherein said fused ring or spiroannulated ring cyclic pro-perfumes may have their rings further substituted by one or more units, said units are independently hydroxyl, $C_1$–$C_{22}$ alkoxy, $C_1$–$C_{22}$ alkyl, $C_1$–$C_{22}$ alkenyl, $C_6$–$C_{22}$ aryl, $C_6$–$C_{22}$ alkylenearyl units, and mixtures thereof. The fused rings may also comprise one or more aromatic rings, including heteroaromatic rings. Examples of aromatic and heteroaromatic rings include benzene, naphthalene, pyridine, quinoline, isoquinoline, etc.

Preferably $R^2$, $R^3$, $R^4$, and $R^5$ are selected such that said units comprise a vicinal diol or 1,3-type diol. For example, when taken together, $R^2$, $R^3$, $R^4$, and $R^5$ derive from diols non-limiting examples of which include 1,2-propanediol, 1,2-butanediol, 1,2-hexanediol, 1,2-octanediol, 1,3-hydroxyacetone, 1,3-octanediol. All of the preceding examples of diols include a hydroxy moiety at the terminus or the alkyl chain. However, as described herein below, non-terminal hydroxy diols are also preferred.

Spacing unit Y is —$CR^6R^7$—, C=O, and mixtures thereof $R^6$ and $R^7$ are independently hydrogen (wherein the moiety —$CR^6R^7$— is a methylene unit), hydroxyl, nitro, nitrilo, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or $R^6$ and $R^7$ as described herein above can be taken together to form a spiroannulated ring or taken together with any $R^2$, $R^3$, $R^4$, or $R^5$ unit to form a fused ring, said spiroannulated or fused ring having from 3 to 8 carbons. In addition, the resulting spiroannulated or fused rings may be further substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof.

The index n is an integer from 0 to 3, preferably 0 or 1, more preferably 0.

For the purposes of the present invention substituted or unsubstituted alkyleneoxy units are defined as moieties having the formula:

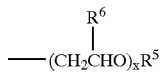

wherein $R^5$ is hydrogen; $R^6$ is hydrogen, methyl, ethyl, and mixtures thereof; the index x is from 1 to about 20.

For the purposes of the present invention substituted or unsubstituted alkyleneoxyalkyl are defined as moieties having the formula:

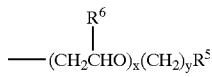

wherein $R^5$ is hydrogen, $C_1$–$C_{18}$ alkyl, $C_1$–$C_4$ alkoxy, and mixtures thereof; $R^6$ is hydrogen, methyl, ethyl, and mixtures thereof; the index x is from 1 to about 20 and the index y is from 2 to about 30.

For the purposes of the present invention substituted or unsubstituted alkylenearyl units are defined as moieties having the formula:

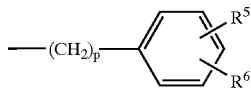

wherein $R^5$ and $R^6$ are each independently hydrogen, hydroxy, $C_1$–$C_4$ alkoxy, nitrilo, halogen, nitro, carboxyl (—CHO; —$CO_2H$; —$CO_2R'$; —$CONH_2$; —CONHR'; —$CONR'_2$; wherein R' is $C_1$–$C_{12}$ linear or branched alkyl), amino, alkylamino, and mixtures thereof, p is from 1 to about 34.

For the purposes of the present invention substituted or unsubstituted aryloxy units are defined as moieties having the formula:

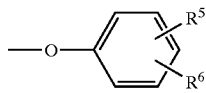

wherein $R^5$ and $R^6$ are each independently hydrogen, hydroxy, $C_1$–$C_4$ alkoxy, nitrilo, halogen, nitro, carboxyl (—CHO; —$CO_2H$; —$CO_2R'$; —$CONH_2$; —CONHR'; —$CONR'_2$; wherein R' is $C_1$–$C_{12}$ linear or branched alkyl), amino, alkylamino, and mixtures thereof.

For the purposes of the present invention substituted or unsubstituted alkyleneoxyaryl units are defined as moieties having the formula:

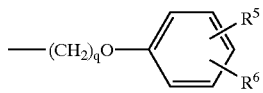

wherein $R^5$ and $R^6$ are each independently hydrogen, hydroxy, $C_1$–$C_4$ alkoxy, nitrilo, halogen, nitro, carboxyl (—CHO; —$CO_2H$; —$CO_2R'$; —$CONH_2$; —CONHR'; —$CONR'_2$; wherein R' is $C_1$–$C_{12}$ linear or branched alkyl), amino, alkylamino, and mixtures thereof, q is from 1 to about 34.

For the purposes of the present invention substituted or unsubstituted oxyalkylenearyl units are defined as moieties having the formula:

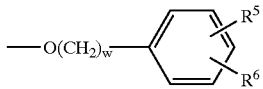

wherein $R^5$ and $R^6$ are each independently hydrogen, hydroxy, $C_1$-$C_4$ alkoxy, nitrilo, halogen, nitro, carboxyl (—CHO; —$CO_2H$; —$CO_2R'$; —$CONH_2$; —CONHR'; —$CONR'_2$; wherein R' is $C_1$-$C_{12}$ linear or branched alkyl), amino, alkylamino, and mixtures thereof, w is from 1 to about 34.

Not wishing to be limited by theory, a formulator wishing to increase the degree of torsional strain in the pro-perfume ring may, however, select a diol having two non-terminus alcohols, for example, 2,3-octanediol or 3,4-octandiol. The increase or decrease in the torsional strain of the cyclic pro-perfume ring provides the formulator with a means for adjusting the rate at which the fragrance raw material alcohol is released by the cyclic orthoester. For example, the two cyclic pro-perfumes having the formulae:

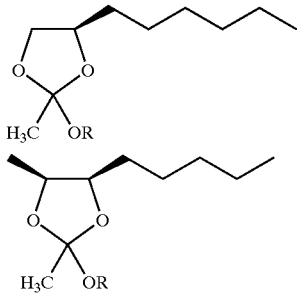

will exhibit different release rates of perfume raw material alcohol ROH due in part to the torsional strain provided by the eclipsing interaction of the methyl group with the alkyl chain.

Fragrance Delivery System

The present invention further relates to fragrance delivery systems comprising:

a) at least one cyclic pro-perfume;
b) optionally one or more pro-perfumes, pro-fragrances, or pro-accords capable of releasing one or more fragrance raw materials, said fragrance raw materials selected from the group consisting of aldehydes, ketones, alcohols, esters, nitrites, nitro compounds, linear, branched and cyclic alkenes, ethers, and mixtures thereof;
c) optionally one or more fragrance raw materials; and
d) the balance carriers and adjunct ingredients.

The pro-perfumes, pro-fragrances, or pro-accords which are combinable with the cyclic pro-perfumes of the present invention are preferably the pro-accords. The term "accord" as used herein is defined as "a mixture of two or more 'fragrance raw materials' which are artfully combined to impart a pleasurable scent, odor, essence, or fragrance characteristic". Therefore a material which is a "pro-accord" is capable of releasing a mixture of fragrance raw materials or a fragrance accord. Non-limiting examples of pro-accords and pro-fragrances include orthoesters, acetals, ketals, orthocarbonates, and the like described herein below.

When formulated into a fragrance delivery system, the cyclic pro-perfumes of the present invention will comprise from about 0.1% to about 99%, preferably from about 1% to about 50% by weight, of said fragrance delivery system.

The fragrance delivery systems of the present invention preferably comprise the pro-accords described herein below. When present, said pro-accords comprise singly or as an admixture from 0.1% to about 99%, preferably from about 1% to about 50% by weight of the fragrance delivery system.

In addition, the fragrance delivery systems of the present invention further comprises carriers, fixatives, and other adjunct ingredients which can be added in any suitable amount or ratio to the cyclic pro-perfumes or the optional pro-accords which comprise the balance of the delivery system. Typical carriers are methanol, ethanol (preferred), iso-propanol, polyethylene glycol, as well as water in some instances. Fixatives serve to lower the volatility of certain top and middle notes in order to extend their contact time on skin. Adjunct ingredients include perfume raw material components which are essential oils and are therefore not a single chemical entity. In addition, the adjunct ingredients may be mixtures of synthetic fragrance raw materials which serve a further purpose in addition to providing a pleasurable odor.

Orthoesters

One class of preferred compounds useful as pro-accords according to the present invention are orthoesters having the formula:

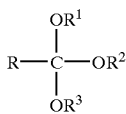

wherein hydrolysis of the orthoester releases fragrance raw material components according to the following scheme:

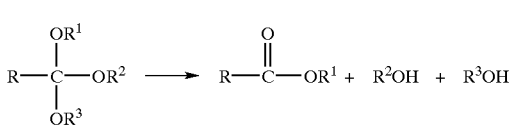

wherein R is hydrogen, $C_1$-$C_8$ linear alkyl, $C_4$-$C_{20}$ branched alkyl, $C_6$-$C_{20}$ cyclic alkyl, $C_6$-$C_{20}$ branched cyclic alkyl, $C_6$-$C_{20}$ linear alkenyl, $C_6$-$C_{20}$ branched alkenyl, $C_6$-$C_{20}$ cyclic alkenyl, $C_6$-$C_{20}$ branched cyclic alkenyl, $C_6$-$C_{20}$ substituted or unsubstituted aryl, preferably the moieties which substitute the aryl units are alkyl moieties, and mixtures thereof, preferably R is hydrogen, methyl, ethyl, and phenyl. $R^1$, $R^2$ and $R^3$ are independently $C_1$-$C_{20}$ linear, branched, or substituted alkyl; $C_2$-$C_{20}$ linear, branched, or substituted alkenyl; $C_5$-$C_{20}$ substituted or unsubstituted cyclic alkyl; $C_6$-$C_{20}$ substituted or unsubstituted aryl; $C_2$-$C_{40}$ substituted or unsubstituted alkyleneoxy; $C_3$-$C_{40}$ substituted or unsubstituted alkyleneoxyalkyl; $C_6$-$C_{40}$ substituted or unsubstituted alkylenearyl; $C_6$-$C_{32}$ substituted or unsubstituted aryloxy; $C_6$-$C_{40}$ substituted or unsubstituted alkyleneoxyaryl; $C_6$-$C_{40}$ oxyalkylenearyl; and mixtures thereof. By the term "substituted" herein is meant "compatible moieties which replace a hydrogen atom". Non-limiting examples of substituents are hydroxy, nitrilo, halogen, nitro, carboxyl (—CHO; —$CO_2H$; —$CO_2R'$; —$CONH_2$; —CONHR'; —$CONR'_2$; wherein R' is $C_1$-$C_{12}$ linear or branched alkyl), amino, $C_1$-$C_{12}$ mono- and dialkylamino, and mixtures thereof Acetals and ketals Another class of compound useful as pro-accords according to the present invention are acetals and ketals having the formula:

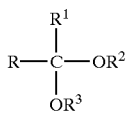

wherein hydrolysis of the acetal or ketal releases one equivalent of aldehyde or ketone and two equivalents of alcohol according to the following scheme:

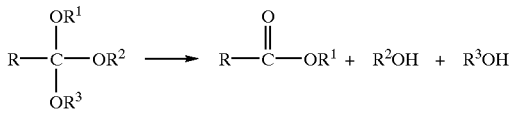

wherein R is $C_1$–$C_{20}$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, preferably the moieties which substitute the aryl units are alkyl moieties, and mixtures thereof $R^1$ is hydrogen, R, or in the case wherein the pro-accord is a ketal, R and $R^1$ can be taken together to form a ring. $R^2$ and $R^3$ are independently selected from the group consisting of $C_5$–$C_{20}$ linear, branched, or substituted alkyl; $C_4$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof By the term "substituted" herein is meant "compatible moieties which replace a hydrogen atom". Non-limiting examples of substituents are hydroxy, nitrilo, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, $C_1$–$C_{12}$ mono- and dialkylamino, and mixtures thereof Orthocarbonates Another class of preferred compounds useful as pro-accords according to the present invention are orthocarbonates having the formula:

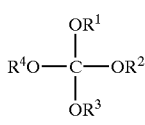

wherein hydrolysis of the orthoester releases the fragrance raw material components according to the following scheme:

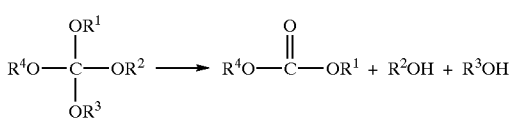

which can continue to hydrolyze and further release two equivalents of one or more fragrance raw material alcohol according to the following scheme:

thereby providing up to four equivalents of fragrance raw material alcohol per equivalent of delivered orthocarbonate, wherein $R^1$, $R^2$, $R^3$, and $R^4$ are independently $C_1$–$C_{20}$ linear, branched, or substituted alkyl; $C_2$–$C_{20}$ linear, branched, or substituted alkenyl; $C_5$–$C_{20}$ substituted or unsubstituted cyclic alkyl; $C_6$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof. By the term "substituted" herein is meant "compatible moieties which replace a hydrogen atom". Non-limiting examples of substituents are hydroxy, nitrilo, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, $C_1$–$C_{12}$ mono- and dialkylamino, and mixtures thereof Fragrance Release Half-life The cyclic pro-perfumes and other pro-accords useful in the fragrance delivery systems of the present invention generally have a delayed release of final fragrance accord in order to achieve the increased fragrance longevity benefits described herein. However, the pro-accords generally also deliver the fragrance accords during a time period useful to the formulator, for example, within a time period desirable to the consumer.

For the purposes of the present invention the pro-accords generally have a "Fragrance Release Half-life" of less than or equal to 12 hours when measured in NaH$_2$PO$_4$ buffer at pH 2.5 and greater than or equal to 0.1 hour when measured in NaH$_2$PO$_4$ buffer at pH 5.3. The "Fragrance Release Half-life" is defined herein as follows.

Pro-accords deliver their corresponding mixture of fragrance raw materials or fragrance accords according to the equation:

Pro-Accord→Accord wherein the accord which is released may be a binary accord or a multiple fragrance raw material accord.

The rate at which the accord is released is defined by the formula:

Rate=k[Pro-accord]

and can be further expressed by the formula:

$$-\frac{d[\text{Pro-accord}]}{dt} = k[\text{Pro-accord}]$$

wherein k is the release rate constant and [Pro-accord] is the concentration of pro-accord. For the purposes of the present invention the "Fragrance Release Half-life", $t_{1/2}$, is related to the release rate constant by the formula:

$$t_{1/2} = \frac{0.693}{k}$$

and this relationship is used for the purposes of the present invention to determine the "fragrance Release Half-life" (FRHL).

Due to the hydrophobic nature of some pro-accords, it is necessary to conduct the determination of $t_{1/2}$ and k in a mixture of 90/10 dioxane/phosphate buffered water. An example of the procedure used to measure the suitability of a pro-accord for use in the fragrance delivery systems at pH 2.5 is as follows. The phosphate buffered water is prepared by admixing 3.95 mL of 85% phosphoric acid ($H_3PO_4$) and 24 g of sodium dihydrogen phosphate ($NaH_2PO_4$) with one liter of water. The pH of this solution is approximately 2.5. Next 10 mL of the phosphate buffer is admixed with 90 mL of dioxane and the pro-fragrance to be analyzed is added. The hydrolysis kinetics are then monitored by conventional HPLC at 30° C.

The pro-accord component of the present invention, in order to assure the stability of acid labile pro-accords, may include a source of reserve alkalinity equivalent to at least 0.001 molar (1 milli-molar) sodium hydroxide. This reserve alkalinity generally serves to prevent premature release of the fragrance raw materials by the pro-accords prior to exposure of the pro-accords to skin. For the purposes of the present invention the term "a reserve alkalinity of at least 0.001 molar" is defined as "the amount of alkaline material present in one liter of the second component when placed in an equivalent volume of water, would produce a hydroxide ion equivalent of 0.001 moles or greater". By way of illustration, 0.0004 g of NaOH present in a 10 mL aliquot of the second component would produce a reserve alkalinity of at least 0.001 molar.

Suitable sources of alkalinity are the alkali metal and alkali earth hydroxides. For example, sodium hydroxide, potassium hydroxide, lithium hydroxide, calcium hydroxide, magnesium hydroxide, sodium carbonate, potassium carbonate, and sodium silicate. However, other suitable sources of alkalinity can be used which are compatible with the pro-accords of the "pro-accord component".

In addition, the fragrance delivery system of the present invention may be suitably use in a fine fragrance composition. Said perfume compositions provide extended fragrance character impressions, and comprise:

A) a pro-accord component comprising:
  i) from 0.1% to 99% by weight, of one or more pro-accords formed from at least one fragrance raw material, said pro-accord releasing upon hydrolysis at least two fragrance raw materials selected from the group consisting of primary, secondary, and tertiary alcohols, aldehydes, ketones, esters, carbonates, and mixtures thereof, provided each pro-accord:
    a) is formed from at least one fragrance raw material having a molecular weight greater than or equal to about 100 g/mol;
    b) has a molecular weight greater than or equal to about 300 g/mol;
    c) has a molecular weight at least two times greater than the lowest molecular weight fragrance raw material which comprises said pro-accord;
    d) has a fragrance release half-life of less than or equal to about 12 hours at pH 2.5 or greater than or equal to about 0. 1 hour at pH 5.3 when measured in $NaH_2PO_4$ buffer;
  ii) the balance carriers, stabilizers, and other adjunct ingredients whereby said pro-accord component is provided with an amount of reserve alkalinity equal to at least 0.001 molar NaOH;
B) a fragrance raw material component comprising:
  i) from 0.1% to about 99% by weight, of a mixture of base note fragrances;
  ii) from 0.1% to about 99% by weight, of one or more top and middle note fragrances;
  ii) the balance carriers, fixatives, and other adjunct ingredients; and
C) from 0.1% to about 99% by weight, of a cyclic pro-perfume component comprising one or more of the cyclic pro-perfumes described herein.

The following are examples of cyclic pro-accords of the present invention which release fragrance raw materials.

EXAMPLE 1

3,4,6tri-O-acetyl-1,2-(ethyllinalyl)orthoacetyl-α-D-glucopyranose

Acetobromoglucose, tetrabutylammonium bromide (0.3 equiv), and ethyllinalool (3 equiv) are suspended in dry collidine and stirred at 65° C. for 3 days. The reaction mixture is diluted with 2 volumes of ether, washed twice with water, and then dried ($MgSO_4$), evaporated, and purified by flash chromatography.

EXAMPLE 2

1,2-(ethyllinalyl)orthoacetyl-α-D-glucopyranose

A solution of 3,4,6-tri-O-acetyl-1,2-(ethyllinalyl) orthoacetyle-α-D-glucopyranose in ethanol is treated with anhydrous $Na_2CO_3$ (0.25 equiv.) and stirred for 6–12 h. After filtration and evaporation of solvent, the resulting material is purified by flash chromatography.

The cyclic pro-perfumes of the present invention are also suitable for use in personal care and personal hygiene compositions. The following are examples of a personnel cleanser composition which is prepared by combining the following ingredients using conventional mixing techniques.

TABLE I

| Ingredients | Weight % | | | |
|---|---|---|---|---|
| | 3 | 4 | 5 | 6 |
| Phase A | | | | |
| Water | QS 100 | QS 100 | QS 100 | QS 100 |
| Disodium EDTA | 0.100 | 0.100 | 0.100 | 0.100 |
| Glycerin | 4.00 | 4.00 | 4.00 | 4.00 |
| Methylparaben | 0.200 | 0.200 | 0.200 | 0.200 |
| $C_{10}$–$C_{30}$ alkyl acrylate crosspolymer[1] | 0.150 | 0.150 | 0.150 | 0.150 |
| Carbomer 954[2] | 0.250 | 0.250 | 0.250 | 0.250 |
| Phase B | | | | |
| Stearic Acid | 0.110 | 0.110 | 0.110 | 0.110 |
| Stearyl alcohol | 0.875 | 0.875 | 0.875 | 0.875 |
| Cetyl alcohol | 0.875 | 0.875 | 0.875 | 0.875 |
| Propylparaben | 0.150 | 0.150 | 0.150 | 0.150 |
| Steareth-2 | — | 0.25 | 0.25 | 0.25 |
| Steareth-21 | — | 0.50 | 0.50 | 0.50 |
| Phase C | | | | |
| Sodium hydroxide[3] | 0.130 | 0.130 | 0.130 | 0.130 |
| Phase D | | | | |
| Diisopropyl sebacate | 1.50 | 1.50 | 1.50 | 1.50 |
| Isohexadecane | 5.00 | 2.00 | 5.00 | 5.00 |
| Mineral Oil[4] | — | 5.00 | — | — |
| Phase E | | | | |
| Phenoxyethanol | 0.5 | 0.5 | — | 0.5 |
| Pro-accord[5] | 1.5 | 1.5 | 2.20 | 1.5 |

TABLE I-continued

| | Weight % | | | |
|---|---|---|---|---|
| Ingredients | 3 | 4 | 5 | 6 |
| Phase F | | | | |
| Glucose amide | 0.96 | 0.96 | 0.96 | 0.96 |

[1] Available as Pemulen ® from B. F. Goodrich Corporation.
[2] Available as Carbomer ® 954 from B. F. Goodrich Corporation.
[3] As a 50% aqueous solution.
[4] Light mineral oil available as Drakeol 5 from Penreco, Dickenson, TX.
[5] Cyclic pro-perfume according to Example 2.

The above Examples 3–6 can be suitably prepared as follows. In a suitable vessel, the Phase A ingredients are mixed at room temperature to form a dispersion and heated with stirring to 70–80° C. In a separate vessel, the Phase B ingredients are heated with stirring to 70–80° C. Phase B is then added to Phase A with mixing to form the emulsion. Next, Phase C is added to neutralize the composition. The Phase D ingredients are added with mixing, followed by cooling to 45–50° C. The Phase E ingredients are then added with stirring, followed by cooling to 40° C. Phase F is heated with mixing to 40° C. and added to the emulsion, which is cooled to room temperature. The resulting cleansing composition is useful for cleansing the skin. The emulsion de-emulsifies upon contact with the skin.

What is claimed is:

1. A pro-perfume having the formula:

$$\text{RO} \underset{R^1}{\overset{R^2}{\diagdown}} \begin{array}{c} O - \overset{R^3}{\underset{|}{C}} \\ (Y)_n \\ O - \underset{R^5}{\overset{|}{C}} - R^4 \end{array}$$

wherein —OR is a unit derived from a fragrance raw material alcohol; $R^1$ is hydrogen, $C_1$–$C_{22}$ alkyl, $C_1$–$C_{22}$ alkenyl, $C_6$–$C_{12}$ aryl, $C_6$–$C_{22}$ alkylenearyl, $C_3$–$C_{20}$ substituted or unsubstituted alkyleneoxyalkyl; $R^2$, $R^3$, $R^4$, and $R^5$ are each independently selected from hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or any two $R^2$, $R^3$, $R^4$, or $R^5$ can be taken together to form a fused ring or spiroannulated ring having from 3 to 8 carbons and optionally one or more ring heteroatoms, said ring is optionally further substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; Y is —$CR^6R^7$—, C=O, and mixtures thereof, wherein $R^6$ and $R^7$ are independently hydrogen, hydroxyl, nitro, nitrilo, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_{3-C30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or $R^6$ and $R^7$ can be taken together to form a spiroannulated ring or taken together with any $R^2$, $R^3$, $R^4$, or $R^5$ to form a fused ring, said spiroannulated or fused ring having from 3 to 8 carbons or optionally one or more ring heteroatoms, said ring further optionally substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; n is from 0 to 3;

provided: when n=0 or 1 and one of $R^2$, $R^3$, $R^4$, $R^5$, $R^6$, or $R^7$ is a hydroxysubstituted $C_1$–$C_6$ alkylene or a hydroxysubstituted $C_6$–$C_{10}$ arylene, then either:

a. said RO— unit must be derived from a fragrance raw material tertiary alcohol; or b. at least one other group selected from $R^2$, $R^3$, $R^4$, $R^5$, $R^6$, or $R^7$ that is attached to a different carbon atom than the carbon atom to which said hydroxysubstituted $C_1$–$C_6$ alkylene or hydroxysubstituted $C_6$–$C_{10}$ arylene is attached must not be H, or c. one of R or $R^1$ must contain at least eleven carbon atoms.

2. A compound according to claim 1 wherein $R^1$ is hydrogen, methyl, ethyl, propyl, iso-propyl, t-butyl, phenyl, substituted phenyl, benzyl, or substituted benzyl.

3. A compound according to claim 2 wherein n is equal to 0.

4. A compound according to claim 3 wherein $R^3$ and $R^5$ are each hydrogen.

5. A pro-perfume having the formula:

$$\text{RO} \underset{R^1}{\overset{R^2}{\diagdown}} \begin{array}{c} O - \overset{R^3}{\underset{|}{C}} \\ \\ O - \underset{R^5}{\overset{|}{C}} - R^4 \end{array}$$

wherein:

a. —OR is a unit derived from a fragrance raw material alcohol;

b. $R^1$ is hydrogen, methyl, ethyl, propyl, iso-propyl, t-butyl, phenyl, substituted phenyl, benzyl, substituted benzyl;

c. $R^3$ and $R^5$ are each hydrogen;

d. $R^2$ and $R^4$ are each independently selected from $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, and $R^2$ and $R^4$ are taken together to form a fused ring having from 4 to 8 carbons and optionally one or more ring heteroatoms, said ring is optionally further substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof.

6. A compound according to claim 4 wherein $R^2$ and $R^4$ are each independently selected from the group consisting of hydrogen, $C_1$–$C_{10}$ substituted or unsubstituted linear alkyl, $C_3$–$C_{30}$ substituted or unsubstituted cyclic alkyl, $C_7$–$C_{10}$ substituted or unsubstituted alkylenearyl, $C_6$–$C_{10}$ substituted or unsubstituted aryl, and mixtures thereof.

7. A compound according to claim 1 wherein said pro-perfume, upon hydrolysis, releases a tertiary alcohol fragrance raw material.

8. A pro-perfume having the formula:

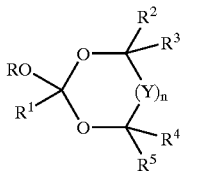

wherein:
a. —OR is a unit derived from a fragrance raw material alcohol;
b. $R^1$ is hydrogen, $C_1$–$C_{22}$ alkyl, $C_1$–$C_{22}$ alkenyl, $C_6$–$C_{12}$ aryl, $C_6$–$C_{22}$ alkylenearyl, $C_3$–$C_{20}$ substituted or unsubstituted alkyleneoxyalkyl;
c. $R^2$ and $R^4$ are each independently selected from $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, $R^2$ and $R^4$ are each taken together to form a fused ring having from 5–7 atoms wherein at least one of said atoms is a heteroatom selected from the group consisting of oxygen, nitrogen, and mixtures thereof;
d. $R^3$ and $R^5$ are each independently selected from hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, and $R^3$, and $R^5$ can be taken together to form a fused ring having from 4 to 8 carbons and optionally one or more ring heteroatoms, said ring is optionally further substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof;
e. Y is —$CR^6R^7$—, C═O, and mixtures thereof, wherein $R^6$ and $R^7$ are independently hydrogen, hydroxyl, nitro, nitrilo, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or $R^6$ and $R^7$ can be taken together to form a spiroannulated ring or taken together with any $R^3$, or $R^5$ to form a fused ring, said spiroannulated or fused ring having from 3 to 8 carbons or optionally one or more ring heteroatoms, said ring further optionally substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof;
f. n is from 0 to 3.

9. A fragrance delivery system comprising:
a) at least one cyclic pro-perfume having the formula:

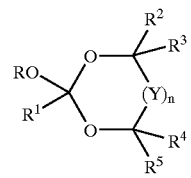

wherein —OR is a unit derived from a fragrance raw material alcohol; $R^1$ is hydrogen, $C_1$–$C_{22}$ alkyl, $C_1$–$C_{22}$ alkenyl, $C_6$–$C_{12}$ aryl, $C_6$–$C_{22}$ alkylenearyl, $C_3$–$C_{20}$ substituted or unsubstituted alkyleneoxyalkyl; $R^2$, $R^3$, $R^4$, and $R^5$ are each independently selected from hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or any two $R^2$, $R^3$, $R^4$, or $R^5$ can be taken together to form a fused ring or spiroannulated ring having from 3 to 8 carbons and optionally one or more ring heteroatoms, said ring is optionally further substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; Y is —$CR^6R^7$—, C=O, and mixtures thereof, wherein $R^6$ and $R^7$ are independently hydrogen, hydroxyl, nitro, nitrilo, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or $R^6$ and $R^7$ can be taken together to form a spiroannulated ring or taken together with any $R^2$, $R^3$, $R^4$, or $R^5$ to form a fused ring, said spiroannulated or fused ring having from 3 to 8 carbons or optionally one or more ring heteroatoms, said ring further optionally substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; n is from 0 to 3;

b) optionally one or more pro-perfumes, pro-fragrances, or pro-accords capable of releasing, upon hydrolysis, one or more fragrance raw materials, said fragrance raw materials selected from the group consisting of aldehydes, ketones, alcohols, esters, nitriles, nitro compounds, linear, branched and cyclic alkenes, ethers, and mixtures thereof;

c) optionally one or more fragrance raw materials; and d) the balance carriers and adjunct ingredients.

10. A composition according to claim 9 wherein said cyclic pro-perfume in (a), upon hydrolysis, releases a tertiary alcohol selected from the group consisting of linalool, ethyllinalool, tetrahydrolinalool, dihydromyrcenol, and mixtures thereof.

11. A composition according to claim 9 wherein said pro-perfumes, pro-fragrances, or pro-accords in (b) are selected from the group consisting of a) orthoesters having the formula:

$$R-\underset{\underset{OR^3}{|}}{\overset{\overset{OR^1}{|}}{C}}-OR^2;$$

b) acetals having the formula:

$$R-\underset{\underset{OR^3}{|}}{\overset{\overset{H}{|}}{C}}-OR^2$$

c) ketals having the formula:

$$R-\underset{\underset{OR^3}{|}}{\overset{\overset{R^1}{|}}{C}}-OR^2$$

d) orthocarbonates having the formula:

$$R^4O-\underset{\underset{OR^3}{|}}{\overset{\overset{OR^1}{|}}{C}}-OR^2;\text{ and}$$

e) mixtures thereof;

wherein R is $C_3$–$C_{20}$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, and mixtures thereof; $R^1$ is hydrogen or R; $R^2$, $R^3$, and $R^4$ are each independently selected from the group consisting of $C_5$–$C_{20}$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ aryl, $C_7$–$C_{20}$ substituted aryl, and mixtures thereof.

12. A composition according to claim 9 wherein at least one cyclic pro-perfume of (a) or at least one pro-perfume, pro-fragrance, or pro-accord of (b) has a fragrance release half-life when measured in $NaH_2PO_4$ buffer of less than or equal to 12 hours at pH 2.5 and great than or equal to 0.1 hours at pH 5.3.

13. A perfume composition having extended fragrance character impressions, comprising:

A) a pro-accord component comprising:
   i) from 0.1% to 99% by weight, of one or more pro-accords formed from at least one fragrance raw material, said pro-accord releasing upon hydrolysis at least two fragrance raw materials selected from the group consisting of primary, secondary, and tertiary alcohols, aldehydes, ketones, esters, carbonates, and mixtures thereof, provided each pro-accord:
      a) is formed from at least one fragrance raw material having a molecular weight greater than or equal to 100 g/mol;
      b) has a molecular weight greater than or equal to 300 g/mol;
      c) has a molecular weight at least two times greater than the lowest molecular weight fragrance raw material which comprises said pro-accord;
      d) has a fragrance release half-life of less than or equal to 12 hours at pH 2.5 or greater than or equal to 0.1 hour at pH 5.3 when measured in $NaH_2PO_4$ buffer;
   ii) the balance carriers, stabilizers, and other adjunct ingredients whereby said pro-accord component is provided with an amount of reserve alkalinity equal to at least 0.001 molar NaOH;

B) a fragrance raw material component comprising:
   i) from 0.1% to 99% by weight, of one or more fragrance raw materials; and
   ii) the balance carriers, fixatives, and other adjunct ingredients; and C) from 0.1% to 99% by weight, of a cyclic pro-perfume having the formula:

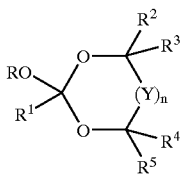

wherein —OR is a unit derived from a fragrance raw material alcohol or thiol; $R^1$ is hydrogen, $C_1$–$C_{22}$ alkyl, $C_1$–$C_{22}$ alkenyl, $C_6$–$C_{12}$ aryl, $C_6$–$C_{22}$ alkylenearyl, $C_3$–$C_{20}$ substituted or unsubstituted alkyleneoxyalkyl, and mixtures thereof; $R^2$, $R^3$, $R^4$, and $R^5$ are each independently selected from hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or any two $R^2$, $R^3$, $R^4$, or $R^5$ can be taken together to form a fused ring or spiroannulated ring having from 3 to 8 carbons and optionally one or more ring heteroatoms, said ring is optionally further substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; Y is —$CR^6R^7$—, C=O, and mixtures thereof, wherein $R^6$ and $R^7$ are independently hydrogen, hydroxyl, nitro, nitrilo, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, or $R^6$ and $R^7$ can be taken together to form a spiroannulated ring or taken together with any $R^2$, $R^3$, $R^4$, or $R^5$ to form a fused ring, said spiroannulated or fused ring having from 3 to 8 carbons or optionally one or more ring heteroatoms, said ring further optionally substituted by one or more $C_1$–$C_{22}$ alkyl, $C_1$–$C_{22}$ alkenyl, $C_6$–$C_{12}$ aryl, $C_6$–$C_{22}$ alkylenearyl units, and mixtures thereof; n is from 0 to 3.

* * * * *